United States Patent
Saurer et al.

(10) Patent No.: US 9,723,984 B2
(45) Date of Patent: Aug. 8, 2017

(54) METHOD AND DEVICE FOR MONITORING BIOMECHANICAL PROPERTIES OF THE EYE

(71) Applicant: TISSOT MEDICAL RESEARCH SA, Le Locle (CH)

(72) Inventors: Alain Saurer, Neuchâtel (CH); Jean-Noël Fehr, Neuchâtel (CH)

(73) Assignee: TISSOT MEDICAL RESEARCH SA (CH)

( * ) Notice: Subject to any disclaimer, the term of this patent is extended or adjusted under 35 U.S.C. 154(b) by 145 days.

(21) Appl. No.: 14/352,170

(22) PCT Filed: Oct. 19, 2012

(86) PCT No.: PCT/CH2012/000240
§ 371 (c)(1),
(2) Date: Apr. 16, 2014

(87) PCT Pub. No.: WO2013/056384
PCT Pub. Date: Apr. 25, 2013

(65) Prior Publication Data
US 2014/0257074 A1  Sep. 11, 2014

Related U.S. Application Data

(63) Continuation of application No. 13/277,379, filed on Oct. 20, 2011, now abandoned.

(51) Int. Cl.
*A61B 3/16* (2006.01)
(52) U.S. Cl.
CPC ...................... *A61B 3/16* (2013.01)
(58) Field of Classification Search
CPC .................. A61B 3/16; A61B 3/125
(Continued)

(56) References Cited

U.S. PATENT DOCUMENTS

| 4,628,938 A | 12/1986 | Lee |
| 4,922,913 A | 5/1990 | Waters, Jr. et al. |

(Continued)

FOREIGN PATENT DOCUMENTS

| AU | 522 834 B2 | 7/1982 |
| EP | 0 061 777 A2 | 10/1982 |
| WO | WO 2012/052765 A2 | 4/2012 |

OTHER PUBLICATIONS

Machine translation of Description of EP0061777, translated Jun. 30, 2014, 31 pages.*

(Continued)

*Primary Examiner* — Michael C Stout
(74) *Attorney, Agent, or Firm* — Ostrolenk Faber LLP

(57) ABSTRACT

A contact lens shaped measuring device comprises a sensor having a protrusion towards the cornea. The measuring device is flexible to a degree that it is flattened by a closing eye lid and the protrusion creates an indentation of the cornea. The force on the protrusion is measured by the sensor. Applying a constant lid acceleration/deceleration model to the movement of the lid and a mechanical model to the cornea, the tension of the cornea is determined and deduced from the force measured with the lid closed, yielding the true intraocular pressure. In an alternative, the protrusion is characterized by a discontinuity in its shape, or the sensor is subdivided, each subsensor being characterized by a protrusion of different shape. With the values obtained as extrema and at the discontinuity or with different protrusions, the tension of the cornea can be obtained by a (linear) extrapolation.

14 Claims, 9 Drawing Sheets

Figure 1:
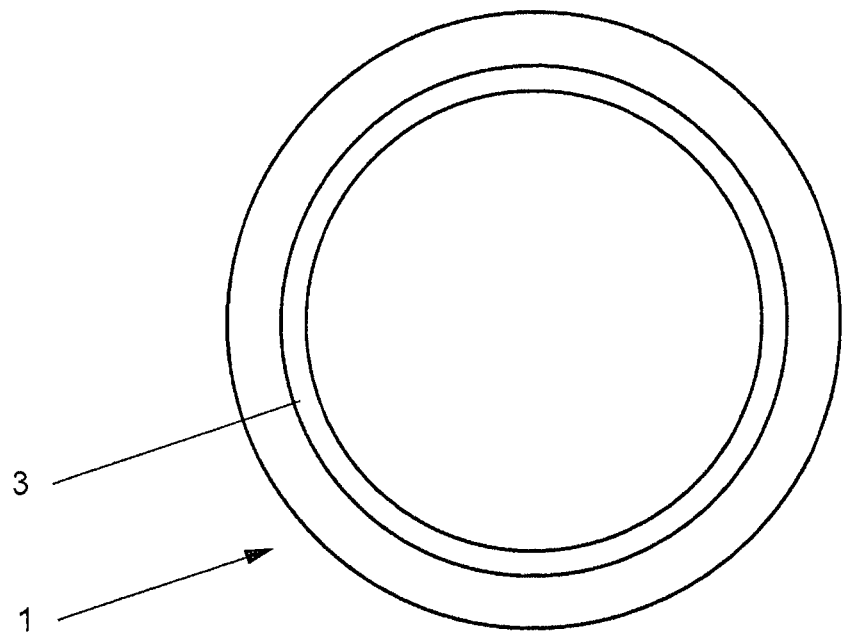

(58) Field of Classification Search
USPC .................................................. 600/398–406
See application file for complete search history.

(56) References Cited

U.S. PATENT DOCUMENTS

| | | | | |
|---|---|---|---|---|
| 5,830,139 | A * | 11/1998 | Abreu | A61B 5/14532 |
| | | | | 600/399 |
| 2008/0259276 | A1 | 10/2008 | Roberts | |
| 2009/0076367 | A1* | 3/2009 | Sit | A61B 3/16 |
| | | | | 600/398 |
| 2011/0015512 | A1* | 1/2011 | Pan | A61B 3/16 |
| | | | | 600/399 |
| 2011/0288395 | A1* | 11/2011 | Elsheikh | A61B 3/16 |
| | | | | 600/398 |
| 2013/0184554 | A1* | 7/2013 | Elsheikh | A61B 3/16 |
| | | | | 600/399 |
| 2014/0016097 | A1* | 1/2014 | Leonardi | A61B 3/0041 |
| | | | | 351/209 |
| 2014/0243645 | A1* | 8/2014 | Leonardi | A61B 3/16 |
| | | | | 600/398 |

OTHER PUBLICATIONS

Machine translation of Claims of EP0061777, translated Jun. 30, 2014, 5 pages.*
International Search Report and Written Opinion dated May 17, 2013 issued in corresponding International patent application No. PCT/CH2012/000240 16 pages.

* cited by examiner

US 9,723,984 B2

METHOD AND DEVICE FOR MONITORING BIOMECHANICAL PROPERTIES OF THE EYE

CROSS REFERENCE TO RELATED APPLICATIONS

The present application is a 35 U.S.C. §371 National Phase conversion of PCT/CH2012/000240, filed Oct. 19, 2012, which claims benefit of U.S. application Ser. No. 13/277,379, filed Oct. 20, 2011, the disclosure of which is incorporated herein by reference. The PCT International Application was published in the English language.

TECHNICAL FIELD OF THE INVENTION

The present invention relates to a method for monitoring biomechanical properties of the eye, more particularly intraocular pressure or characteristics of the cornea, and a device for measuring eye properties of that kind.

BACKGROUND OF THE INVENTION

Conventionally, IOP (cf. Glossary) is measured by applanation of the cornea, e.g. by the Goldman applanometer. Devices of this type exert pressure centrally on the cornea up to a predefined applanation and measure the force required. However, due to the central impact on the cornea, a significant dependence on the curvature of the cornea and its stiffness exists.

Recently, pressure sensors have been developed measuring the pressure or force exerted in a peripheral region of the cornea. One such sensor is described in British patent application 1017637.8 in the name of the University of Dundee et al. which is not yet published. The pressure sensor is a contact lens with a circumferentially embedded pressure sensor. The pressure sensor bears toward the cornea an elevation. If the lid closes over the contact lens, it is flattened and the elevations are pressed on the cornea. On the basis of a suitable calibration, which accounts for individual mechanical properties of the eye and the lid, the IOP can be monitored over extended periods, e.g. 24 hours.

The front side of the sensor portion, i.e. opposite the cornea, may be constituted by a material significantly stiffer than the cornea so that the pressure of the lid is transmitted to the sensor without significant deterioration.

Generally, the sensor is of the type of a variable capacitor coupled to an inductance to constitute a resonance circuit. The inductance serves as the antenna so that the resonance frequency can be wirelessly determined.

For example, an eyeglass frame may be provided with a suitable antenna and the emitter electronics may be implemented in the frame. Thereby, monitoring is possible with only a minimum impairment to the monitored person.

However, the requirement of an adaptation and periodical recalibration of the system remains, which is burdensome and expensive.

SUMMARY OF THE INVENTION

Therefore it is an object of the present invention to provide a method and device which require less calibration efforts.

Another object is to provide method and device allowing the monitoring of other properties of the eye than the IOP.

Method and devices attaining at least the first object are defined in the independent claims. The further claims define preferred embodiments thereof.

Such a method is a method for monitoring biomechanical properties of the eye, using a measuring arrangement which comprises a measuring device designed to be worn in the manner of a contact lens, the measuring device comprising a force detector in operative engagement with a protrusion directed towards the cornea of an eye once the measuring device is applied to the eye, the measuring device being flexible in order to be pressed against the cornea by a lid of the eye moving over the measuring device, wherein the method comprises the following steps:

measuring and storing force values and indication of time when the force values occurred;

determining the time $t_{start}$ when the force values start to be significantly greater than zero, time $t_{End}$ at which the force values after $t_{start}$ are no longer substantially greater than zero, equivalent to the times when the protrusion first gets in contact with the cornea or respectively disconnects therefrom;

determining a maximum force value between $t_{start}$ and $t_{End}$ in order to determine the phases of eye closing, eye being closed position, and eye opening;

deriving from the force values and the corresponding time values between $t_{start}$ and $t_{End}$ a value indicative of the tension of the cornea;

providing the shape of the protrusion with at least one discontinuity so that at least one significant step in the force values is observed, with the step being attributable to an indentation depth predefined by the discontinuity; and in addition to providing a protrusion as set forth above, performing an extrapolation, preferably a linear extrapolation towards indentation depth 0, or a non-linear fit using at least two of the measured value pairs of (a) maximum force and corresponding indentation depth; and (b) the pairs of force values and corresponding indentation depths defined by the at least one discontinuity.

Preferred developments thereof are a method wherein at least one of the following is performed:

the shape of the protrusion is provided with at least one discontinuity so that at least one significant step in the force values is observed, with the step being attributable to an indentation depth predefined by the discontinuity the movement of the lid is determined based on a movement of constant deceleration and acceleration;

the tension of the cornea is determined by determining the parameters of a model of the cornea by inserting measured force values and time values, or values derived therefrom, in equations of the model.

The object is attained by a device for measuring properties of the eye, substantially shaped as a contact lens, wherein the device comprises a sensor of annular shape and peripherally arranged and having at least one protrusion directed towards the eye when applied to the eye, the device having such an overall flexibility that a lid closing over the device can deform it sufficiently to indent the cornea by the protrusion, wherein the protrusion has at least two portions of different heights.

An alternate device is a device for measuring properties of the eye, substantially shaped as a contact lens, wherein the device comprises a sensor of annular shape and peripherally arranged and having a protrusion directed towards the eye when applied to the eye, the device having such an overall flexibility that a lid closing over the device can deform it sufficiently to indent the cornea by the protrusion, wherein the protrusion has flanks which comprise at least one step creating a transition zone from a larger protrusion to a smaller protrusion.

A further alternate device is a device for measuring properties of the eye, substantially shaped as a contact lens, wherein the device comprises a sensor of annular shape and peripherally arranged and having a protrusion directed towards the eye when applied to the eye, the device having such an overall flexibility that a lid closing over the device can deform it sufficiently to indent the cornea by the protrusion, wherein the sensor is subdivided into at least two subsensors, the subsensors having protrusions of different sizes, so that the subsensors touch the cornea at different times when the lid closes over the device.

Further variants and developments of the method and the device are given in the description and the claims.

DESCRIPTION OF PREFERRED EMBODIMENTS

The invention will be further described by preferred embodiments with reference to the Figures.

Figure 4:
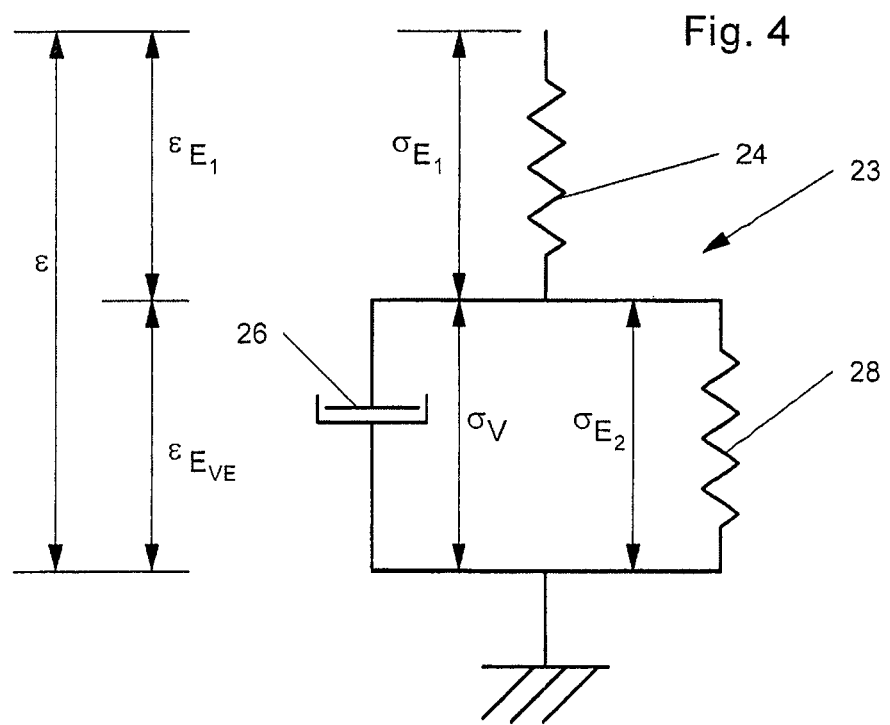
Figure 2:
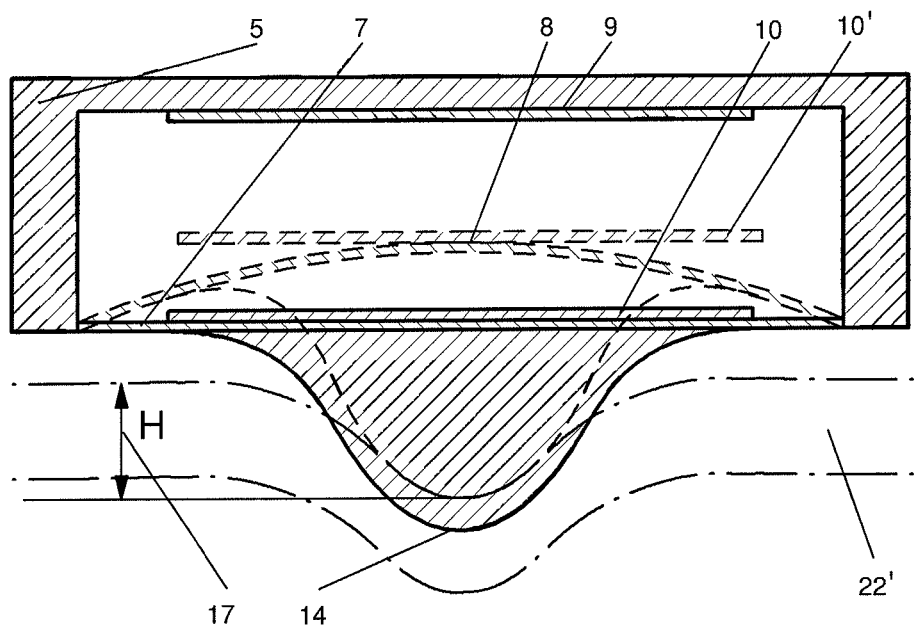
Figure 3:
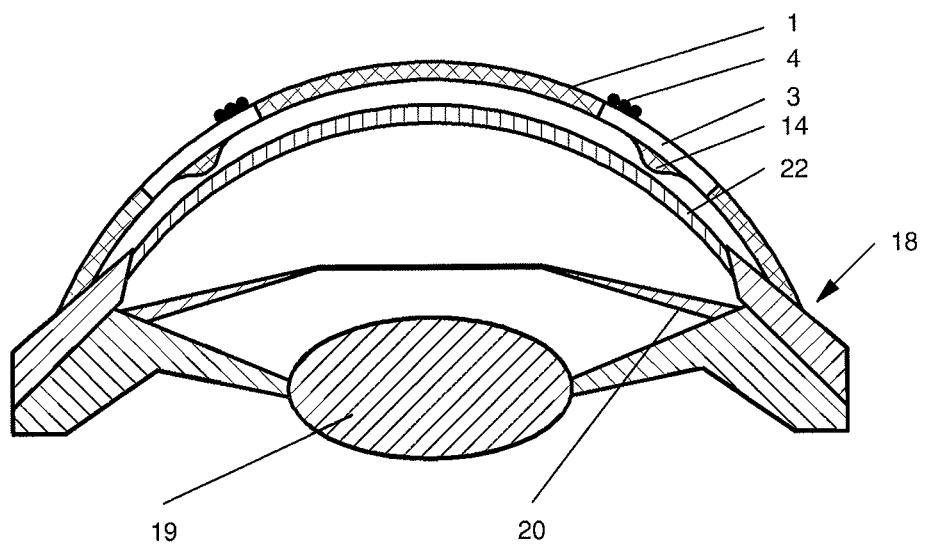
Figure 5:
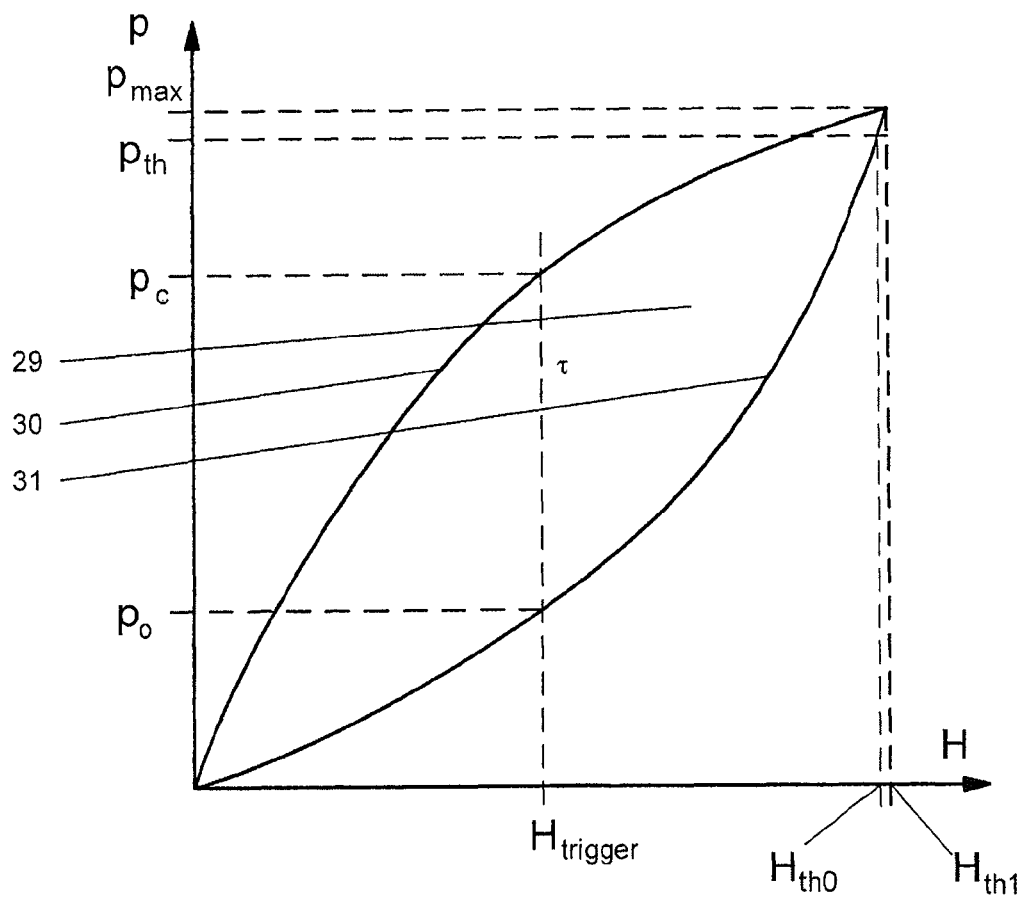
Figure 11:
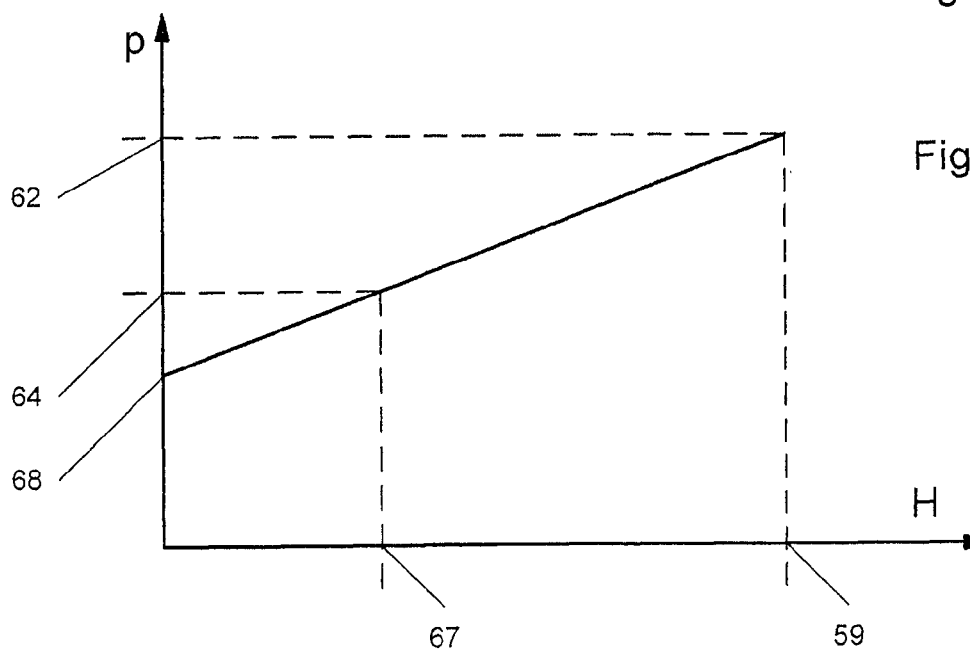
Figure 6:
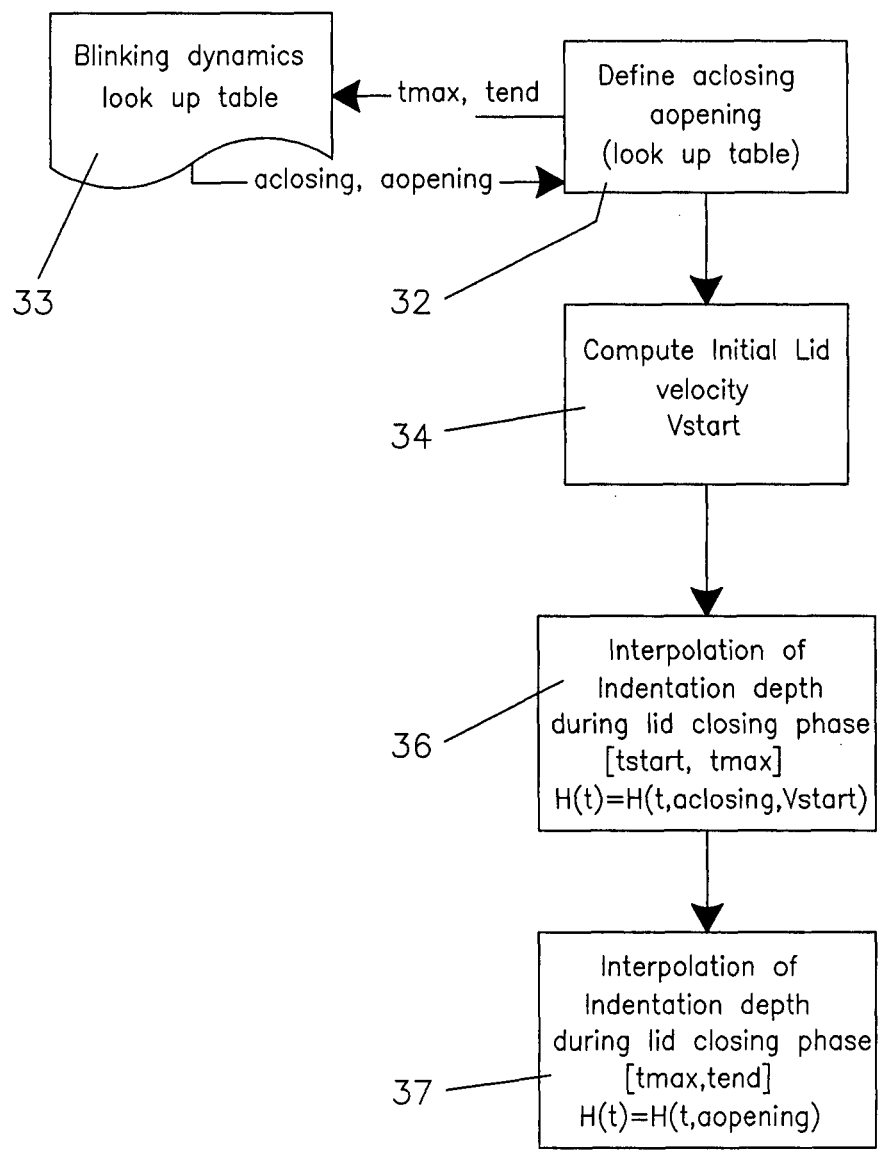
Figure 7:
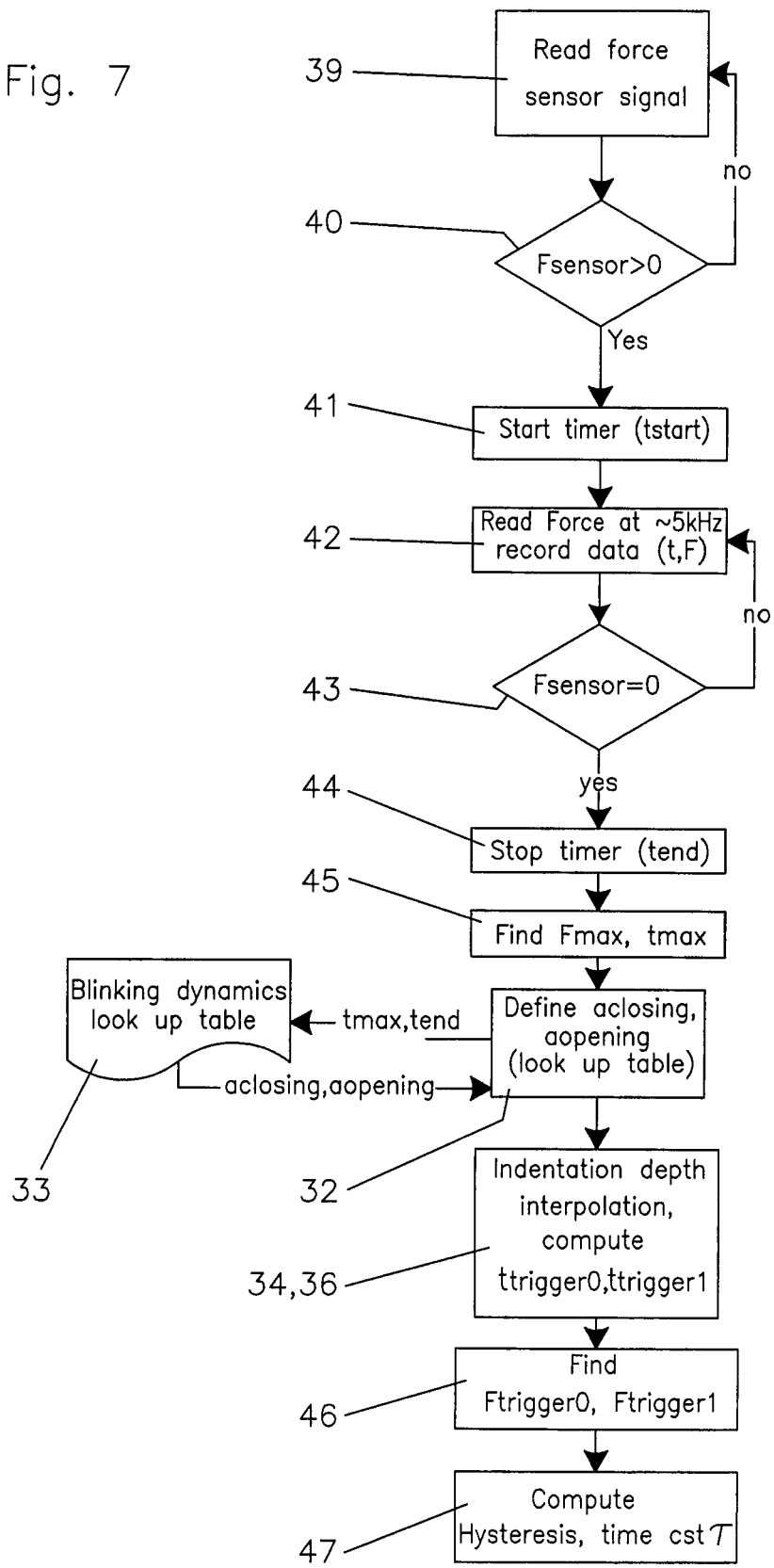
Figure 8:
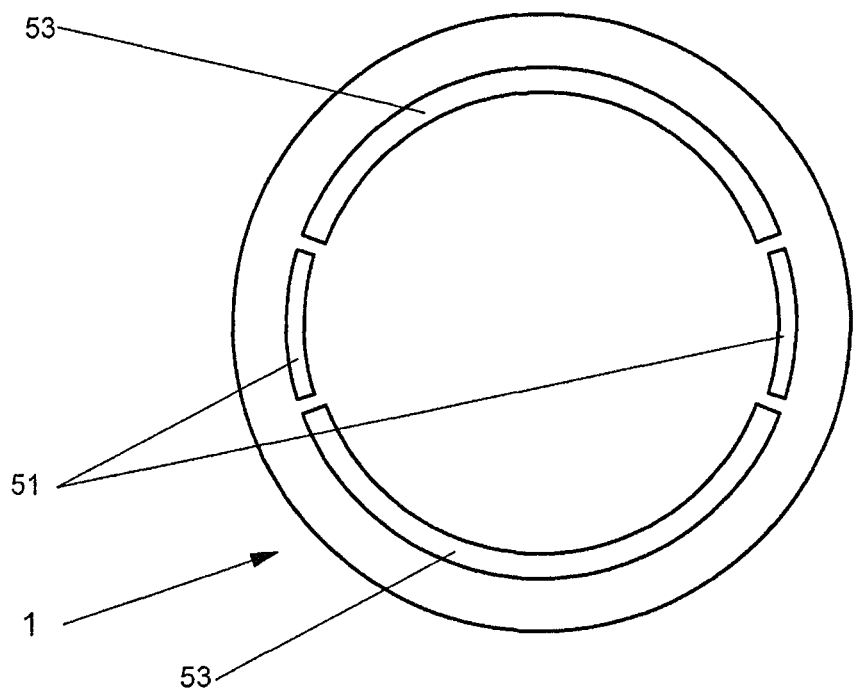
Figure 9:
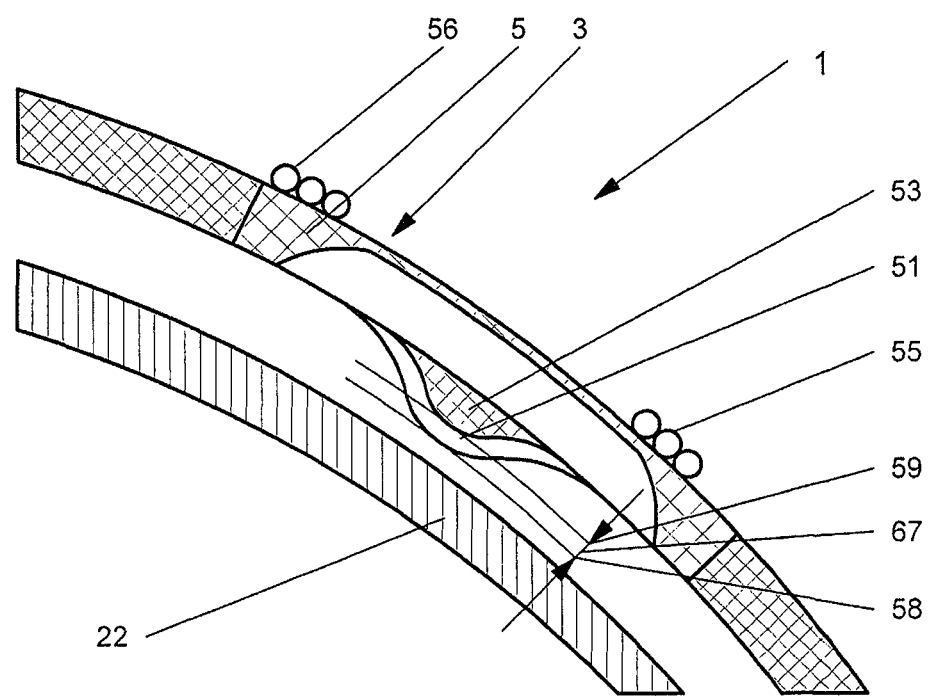
Figure 10:
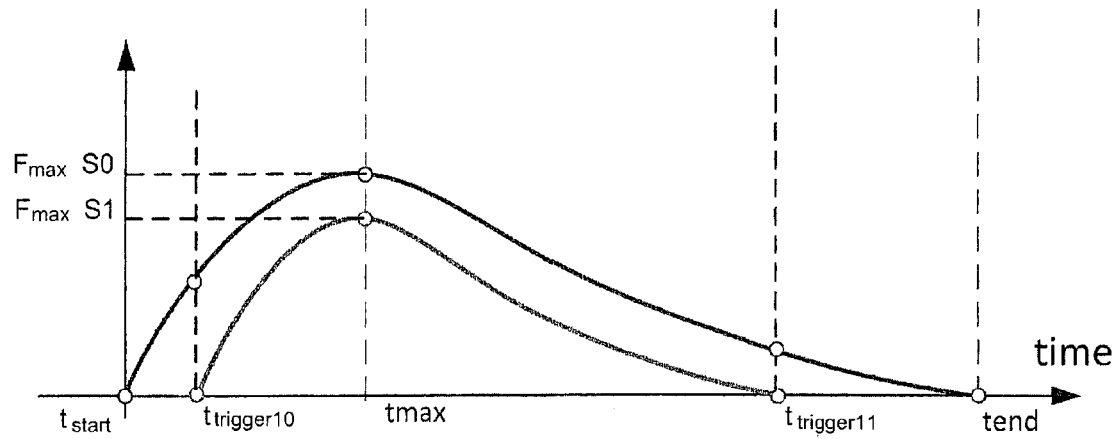
Figure 12:
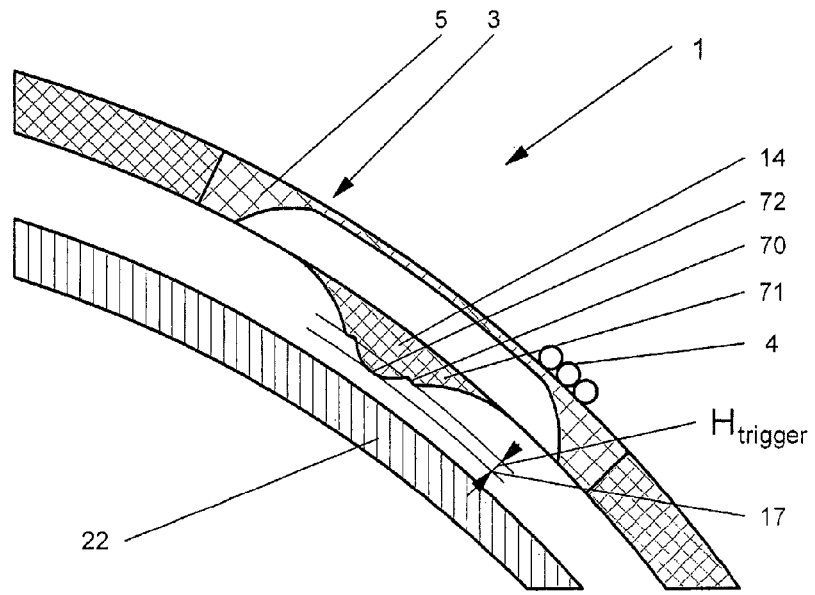
Figure 13:
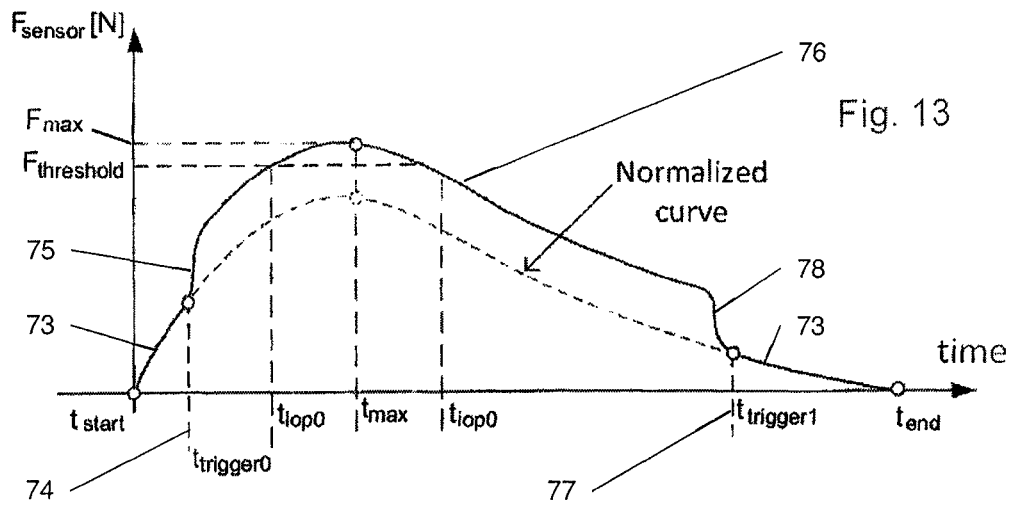
Figure 15:
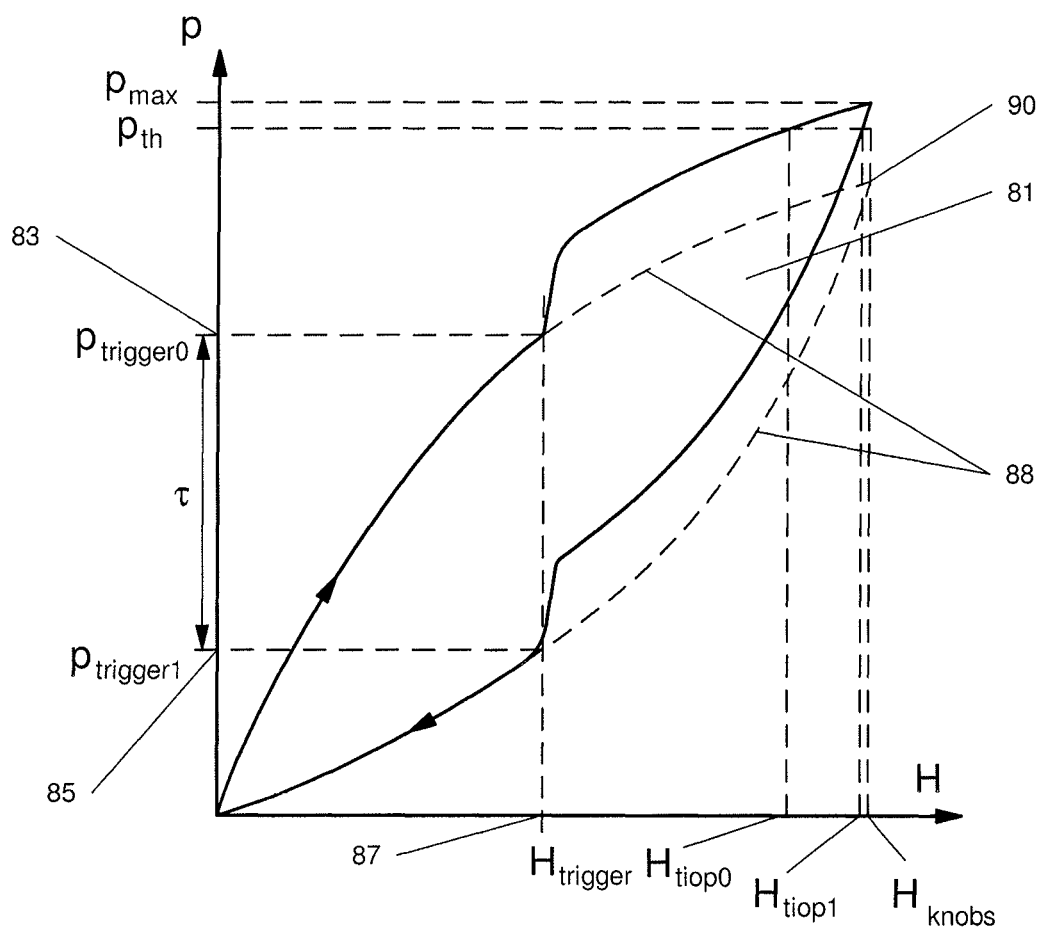
Figure 14:
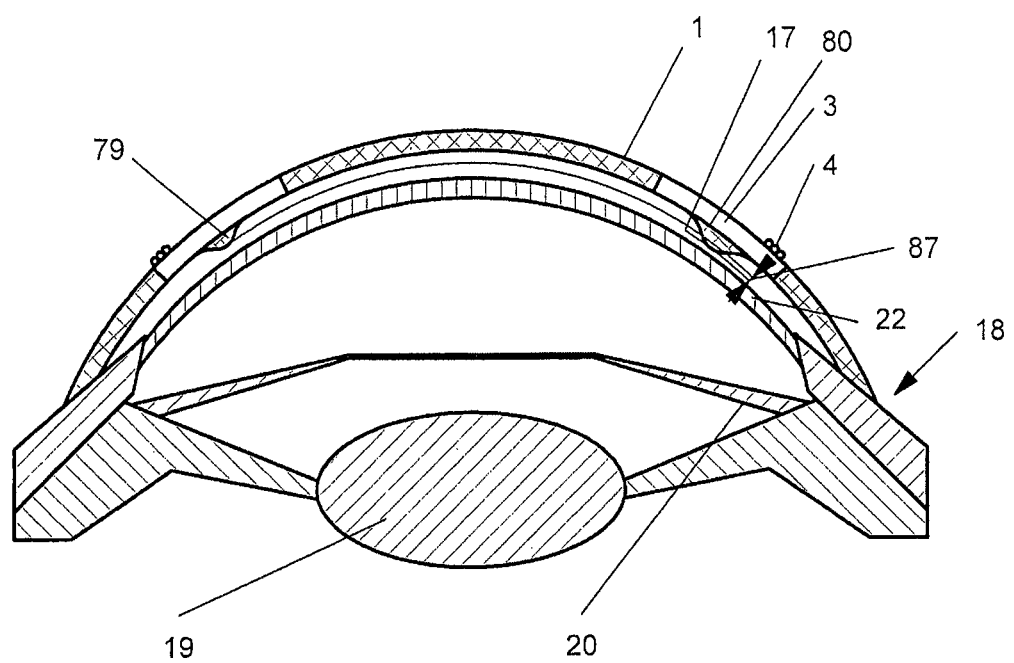

FIG. 1 Top view of a monitoring lens;
FIG. 2 Enlarged cross-section through a sensor, with indented situation indicated by broken lines;
FIG. 3 Cross-section through an eye with monitoring lens;
FIG. 4 Mechanical model;
FIG. 5 Hysteresis-diagram for knob;
FIG. 6 Flow diagram: Indentation depth interpolation according to constant acceleration model for the eye lid;
FIG. 7 Flow diagram: Computation of hysteresis, interpolation only;
FIG. 8 Top view of lens with two sensors;
FIG. 9 Partial cross-section of the sensor of FIG. 8; enlarged;
FIG. 10 Force-time diagram of the lens of FIG. 8;
FIG. 11 Extrapolation diagram;
FIG. 12 Cross-section of knob with transition;
FIG. 13 Force-time diagram of knob of FIG. 12;
FIG. 14 Cross-section through monitoring lens with sensor having varying knob shape;
FIG. 15 p-H-diagram of sensors with transition.

DESCRIPTION

FIG. 1 shows a "monitoring lens" 1, i.e. a contact lens with a sensor 3. The sensor 3 is an annular arrangement of a pressure sensing device. Preferably, it is a capacitive sensor. A coil 4 is arranged as an annular winding on the outside. Sensor 3 and coil 4 build a resonance circuit with a resonance frequency dependent on the force exerted on the sensor. A schematic cross-section through sensor 3 is shown in FIG. 2. An essentially U-shaped rigid frame 5 is closed by a membrane 7. On the bottom of the frame 5 (upper side in FIG. 2), one electrode 9 is provided. A second electrode 10 is attached to the interior face of membrane 7. Preferably, (and as shown in dashed lines as 10' in the indented state,) the second electrode 10 is fixed (glued, soldered or the like) to the center of membrane 7 so that its flexibility is less reduced. If the second electrode 10 is attached to the membrane by its entire surface, the membrane-electrode stack will have a significantly increased stiffness. Furthermore, by the only quite small attachment zone 8, it is avoided that the second electrode 10 is bent in the indented state as indicated by 10' in FIG. 2.

On the exterior face of membrane 7, a knob 14 is provided. As it is to be pressed on the cornea 22 (FIG. 3), it is of a soft, resilient and biocompatible material like silicone or a hydrogel.

Further indicated by dash-dotted lines in FIG. 2 is the indented cornea 22' of an eye. The indentation occurs under the influence of the lid when closed, either by blinking or during sleep.

The height 17 of the knob 14 (FIG. 2) and the displacement of the membrane are emphasized for illustration purposes. Movement of the membrane reduces the indentation of the cornea and the forces exerted, hence reduces the signal amplitude.

The knob is to create indentation of the cornea in the magnitude of micrometers, hence its shape may have a generally flatter aspect, cf. GB 1017637.8.

This minimal indentation of the cornea constitutes an important advantage of the monitoring lens over the prior art applanometers. Due to the minimal impact on the eye considered in its entirety, it is reasonable to assume that the true IOP is not influenced by the measurement, i.e. is considered as constant with regard to the time needed for a spontaneous blink, i.e. the time scale of the dynamic measurement where during a blink of the lid, a measurement cycle is performed.

FIG. 3 shows a partial section through an eye 18 (lens 19; iris 20; cornea 22) bearing a monitoring lens 1 with sensor 3. Noteworthy in the passive state, the knob 14 does not touch the cornea.

A basic finding in the context of the present invention consists in that during closing, the lid is first accelerated by a constant value, then slowed down by substantially the same value.

The same applies during the opening of the lid, but with lower acceleration values.

Furthermore, the mechanical behavior of the cornea during indentation can be described by a viscoelastic model 23 (FIG. 4) (D. H. Glass, C. J. Roberts, A. S. Litsky, P. A. Weber, A Viscoelastic Biomechanical Model of the Cornea Describing the Effect of Viscosity and Elasticity on Hysteresis, IOVS 49 (2008) 3919-3926.).

In series to the first elastic element 24 lay in parallel the viscous element 26 and the second elastic element 28. These elements represent the viscoelastic behavior of the cornea. The model explains the hysteresis in a curve 29 showing the measured pressure p vs. indentation H as shown in FIG. 5.

With measuring the pressure $p_{trigger}$ at a given indentation $H_{trigger}$ while closing (upper branch 30) and opening (lower branch 31) the eye, having respectively $p_c$ and $p_o$, the hysteresis $T = \Delta p_{hy} = p_c - p_o$ can be determined. Thereby, viscoelastic and other properties of the cornea and the eye are accessible additionally to the IOP.

Furthermore, the model 23 allows calculation of the contribution $p_{cornea}$ to the uncompensated pressure $IOP_{raw}$. The model 23 is characterized by the following equations (cf. FIG. 4):

$$\sigma = \sigma_V + \sigma_{E_2} \ ( = \sigma_{E_1}) \tag{1}$$

$$\varepsilon = \varepsilon_{E_1} + \varepsilon_{VE} \ (\varepsilon_{VE} = \varepsilon_V = \varepsilon_E) \tag{2}$$

$$(\sigma_{E_1} =) \ \sigma = E_1 \varepsilon_{E_1} \tag{3}$$

$$\sigma_V = \eta \frac{d\varepsilon_{VE}}{dt} \tag{4}$$

-continued $$\sigma_{E_2} = E_2 \varepsilon_{VE} \quad (5)$$

With σ corresponding to p(t) and ε to H(t), the contribution $p_{cornea}$ during the period $t_{IOP0}$ to $t_{IOP1}$, i.e. on the measured pressure during the quasi-steady state while the lid is closed, can be determined and in consequence the true or compensated IOP be obtained. In practice, a non-linear fit algorithm may be used to resolve the equations of the model.

A further property of the monitoring lens 1 is that its flattening is quantitatively correlated with the movement of the lid. In other terms, the position $s_{lid}$ of the lid in the direction of the opening/closing movement is a measure for the distance between cornea 22 and frame 5 and therefore also a measure for the indentation H of the cornea 22 by the knob 14 once the knob 14 touches it. Preferably, when the lid is entirely closed, the frame 5 touches the cornea 22, and a maximum or steady-state indentation $H_{knob}=H_{knob,max}$ occurs.

Example 1

In order to determine the characteristic values of the hysteresis curve 29 of FIG. 5, it is considered that the acceleration values during opening ($a_{open}$) and closing ($a_{close}$) of the lid can be derived from the delay between occurrence of maximal force, corresponding to the closed lid, and the time when the force is zero again, i.e. the lid is opened to a degree that the knob 14 no longer exerts a sensible force on the cornea. As explained above, the indentation depth H is then accessible by interpolating the position of the lid using the general equation $$s_{lid} = \tfrac{1}{2} a t^2 v_0 t + s_{lid0} \quad (6)$$

with
a: the acceleration of the lid
$s_{lid}$: position of the lid at time t
$s_{lid0}$: position of the lid at t=0: on closing: $s_{lid0}=0$; on opening: $s_{lid0}$=final position of the when closed, i.e. at $t_{IOP0}$.
t: time
$v_0$: the velocity of the lid at time t=0 defined as the moment when the knob 14 hits the cornea 22 on lid closing; on lid opening: $v_0=0$ For the application of this equation, it shall be recalled that the measured time interval covers only the phases when the lid is decelerating during the closing movement and accelerating during the opening movement.

The relation between H and s $$H=f(s_{lid}) \quad (7)$$

is determined by calibration of the lens 1 and stored. In practical terms, $s_{lid}$ may also correspond to the angle of the lid.

The force F(t) sensed by the knob 14 when indenting the cornea is generally unambiguously related to the pressure p although the contact surface varies with the indentation depth H. The relationship between F(t) and p(t) for a given knob shape can be empirically determined and used as a lookup table or a numerically determined function, e.g. a polynomial, or a set of functions, e.g. a (cubic) spline. Empirically, rounded shapes of the knob have been found suitable, i.e. knobs with rounded apex (obviously also avoiding irritations of the cornea).

Furthermore, it is possible to determine a shape of the knob where the dependence of pressure is linearly dependent on the measured force, hence the following equation applies:

$$p(t)=c_p F(t) \quad (8)$$

with
$c_p$ a constant
which significantly simplifies the calculations.

In another approach, the pressure may additionally be dependent on the interpolated indentation depth, e.g.

$$p(t)=g(H(t))F(t) \quad (9)$$

with
g(H(T)): function of H(t), characteristic for the knob; defined analytically or by discrete values and interpolated as necessary; may be determined by (FEA) simulation or measurement;

The shape is, with sufficient precision, independent of an individual eye. The exact shape can be found e.g. by numeric methods on the basis of mechanical properties of the cornea, e.g. by Finite Element Analysis FEA.

The evaluation of the sensor signal is shown by flow diagrams in FIGS. 6 and 7. The sensor furnishes its values with a sufficient high rate to an evaluation device, e.g. constituted by an embedded controller, possibly integrated in glasses, or a separate station to which data received by the monitoring circuitry in the glasses are continuously (wireless) or periodically transferred. Hence, the data may be locally stored and transferred later on to a evaluation station, or immediately evaluated.

Eyelid closing occurs within typically 75 ms, with the period used for the measurement ($t_{start}$ to $t_{IOP0}$) in the range of 1 to 3 ms, and lid opening within about 3 times those periods (i.e. totally about 225 ms, $t_{IOP1}$ to $t_{end}$ about 3 to 9 ms), while the lid remains typically closed during a spontaneous blink for about 16 ms. In view of the movement of the lid, the force data have to be sampled sufficiently fast, at least 5 values are required per branch 30, 31 of the hysteresis curve. As transfer rate from the sensor to the emitter/receiver is limited, it is preferred to base the interpolation for determining the acceleration values from the opening phase which occurs over a significantly longer period. Empirically and from theoretical considerations, a data acquisition rate of about 5 kHz is sufficient. Higher rates tend to improve the performance.

The time $t_{max}$ when the lid is closed is determined as the point in time where the force signal is at its maximum $F_{max}$. Practically, as the period the lid is closed is taken as the interval from $t_{IOP0}$ to $t_{IOP1}$ where the force F(t) remains above a predetermined threshold. As such, it is taken e.g. a percentage of the maximum signal. The percentage is at most 10%, preferably at most 5%, and most preferably at most 2%, i.e. the threshold $F_{th}$ is defined to be at least 0.9 $F_{max}$, or 0.95 $F_{max}$ or 0.98 $F_{max}$.

The time period $t_{End}-t_{IOP1}$ ($t_{End}$: point in time where the sensor signal gets 0 again, i.e. the knob no longer exerts a measurable force of the cornea) is used 32 as an index in a generic lookup table 33 (FIG. 6). The table 33 furnishes the values of $a_{open}$ and $a_{close}$ for the acceleration during opening of the lid and the deceleration during closing of the lid. According to the preferred embodiment, the knobs are designed such that they measurably contact the cornea only in the periods where the lid is slowing down in lid closing and accelerating in lid opening.

Using $a_{close}$ and the times $t_{start}$ (time when a measurable force signal first occurred, i.e. the knob starts to exert pressure on the cornea) and $t_{IOP0}$ (time where the force signal passes $F_{th}$, indicative of that the lid is closed and its movement has stopped), the lid velocity $v_{close0}$ at $t_{start}$ is determined 34:

$$v_{start}=a_{close}(t_{IOP0}-t_{start}) \quad (10)$$

Now, the indentation depth H(t) is determined 36 resp. 37 for closing and opening based on the positions of the lid which is given by the equations:

$$s_{close} = v_{start}(t - t_{start}) - \tfrac{1}{2} a_{close}(t - t_{start})^2; \quad (11)$$

$$s_{open} = \tfrac{1}{2} a_{open}(t - t_{IOP1})^2 + s_0; \quad (12)$$

with $s_0$ the closed position of the lid, e.g. given as the final value of $s_{close}$ for the closing resp. opening movement of the eye.

The pressure p(t) is determined on the basis of the sensor signal, i.e. the force exerted on the knob by the eye.

With the measured indentation H(t), the known time t when these indentations have been measured, and p(t), the hysteresis curve p(H(t)) can be constructed and the true IOP can determined by compensating the influence of the cornea on the measured uncompensated $IOP_{raw}$ which is the pressure measured as an average in the quasi-steady state period from $t_{IOP0}$ to $t_{IOP1}$. This separation is done by considering the IOP as a constant on the measurement time scale, i.e. for the duration of a blink as set forth above.

For the non-linear fit, the period $t_{start}$ to $t_{End}$ is subdivided in three segments:

A) Lid closing, increasing force: $t_{start}$ to $t_{IOP0}$
B) Lid about closed, force about constant: $t_{IOP0}$ to $t_{IOP1}$
C) Lid opening, force decreasing: $t_{IOP1}$ to $t_{End}$ A) and C) are characterized by that the sensor frame 5 is not yet or no more in touch with the eye 18, although the cornea is indented. During these phases, the viscoelastic model 23 is applied.

In phase B, however, the frame 5 touches the cornea 22. Therefore, independently of the position of the lid (which is now closed), indentation depth is assumed to be constant because the sensor is steady with respect to the eye, and the viscous component has a sufficiently short relaxation, that its contribution can be neglected. In this phase, the pressure component of the cornea is determined by the elastic elements $E_1$ and $E_2$ only.

During phases A and C, based on the viscoelastic model, the non-linear fit can be determined on the basis of the [H(t), p(t)] value pairs yielding the parameters $E_1$, $E_2$, and $\eta$ of the model. Using $E_1$ and $E_2$ for calculating the reduction of the IOP by the tension of the cornea:

$$P_{cornea} = \frac{E_1 E_2}{E_1 + E_2} \left[ \frac{H_{knob}}{\alpha_{anat}} \right] \quad (13)$$

with $\alpha_{anat}$ a constant;
and $$IOP = IOP_{raw} - p_{cornea} \quad (14)$$

furnishes the true IOP.

For the non-linear fit, the equations given above can be used in a numerical equation solver or they can be combined to a reduced set of equations, down to only one equation, and then subjected to a usual non-linear fitting algorithm. As a criterion for approximating the correct solution, the principle of least squares error is suitable.

Starting with the mentioned equations, the following particular solution of this system of differential equation can be derived:

$$P_{cornea}(t) = \frac{H(t) E_1}{\alpha_{anat} \left[ 1 + \frac{E_1}{E_2}(1 - e^{-t/\tau}) \right]} \quad (15)$$

where

H (t) depth of indentation of cornea at time t
$\tau = \eta_1 / E_1$ hysteresis constant In deriving the formula, it is supposed that the model of constant acceleration of the lid is applicable and that the reaction force of the monitoring lens is negligible with respect to the force the lid exerts on the lens.

Applying a non-linear fit to this formula in connection with equation 14 and using the results of the measurement (measured pressure on the cornea indentation depth at different times t and the hysteresis constant $\tau$) yields $E_1$ and $E_2$.

Furthermore, a viable approach is to set $E_1 = E_2$ (D. H. Glass, Characterization of the Biomechanical Properties of the in vivo Human Cornea (Thesis), Ohio State University, 2008, cf. p. 59).

The hysteresis constant $\tau$ can be determined by determining the pressure at equal indentations $H_{trigger}$ during opening and closing the eye. For determining the values for these indentations, interpolation techniques known per se may be used. The hysteresis $\tau$ is supposed to furnish information of the healthy state of the cornea and the eye and is used in the non-linear fit.

FIG. 7 shows the flow diagram of calculating T. The initial steps are identical with the determination of IOP explained above, although not shown in FIG. 6:

The force signal of the sensor is read 39 until it significantly deviates 40 from zero. This point in time is defined 41 as $t_{start}$. Force signals $F_{sensor}$ are recorded and stored 42 at 5 kHz until it is determined 43 that it no more deviates significantly from zero. This point in time is stored 44 as $t_{end}$.

In the recorded data duples ($F_{sensor,i}$, t), the maximum $F_{sensor,max}$ value is searched 45, and the corresponding time $t_{max}$ is recorded. The data are postprocessed for determining properties of the eye or values indicative of its health state, in particular the IOP as set forth above.

Next step is again determining 32 the parameters of the movement of the lid using the look-up table 34 and therefrom 36 the indentation depths $H_i$ for the $F_i$ values.

Furthermore, the time $t_{trigger0}$ is determined in a predefined position between $t_{start}$ and $t_{max}$ (or as an alternative $t_{IOP0}$) and, and the corresponding point in time $t_{trigger1}$ for the lid opening phase between $t_{max}$ (alternative: $t_{IOP1}$) and $t_{end}$ as the point in time where the same indentation as at $t_{trigger0}$ occurs, wherein intermediate values are interpolated. Alternatively, instead of defining $t_{trigger}$, $H_{trigger}$ may be determined. Suitable values for $t_{trigger0}$ are the middle of the mentioned intervals, or $H_{trigger} = \tfrac{1}{2} H_{knob,max}$ (max. indentation depth).

For $t_{trigger}$ or $H_{trigger}$, the force values $F_{trigger0}$ and $F_{trigger1}$ during closing resp. opening the eye are calculated 46 using interpolation as required. The difference $F_{trigger0} - F_{trigger1}$ yields 47 a measure of $\tau$.

In a preferred variant, the threshold force value $F_{th}$ is determined in an autocalibration cycle. The device determines whether the eye is closed longer than a predefined time $t_{th}$. The start and stop criterion is whether the force is greater than zero resp. zero again. Then the initial and final values representing closing and opening the eye are discarded. The resulting period is significantly longer than the usual time for these movements, e.g. at least ½ s or at least 1 s. The force values of this period of closed eye are postprocessed. Preferably, an averaging is included. $F_{th}$ is then set to be a small percentage lower than the obtained steady state force value, cf. above.

For an autocalibration, the patient may be asked to close the eyes for a few seconds, or periods of extended lid closure may be used and automatically detected, e.g. sleep. Manual triggering and controlling is possible as well, where even discarding of initial and final values may be avoided.

Accordingly, $t_{th}$ may be a few seconds, e.g. at least 2 s, preferably at least 5 s or even at least 10 s.

Example 2

In order to avoid the computational effort of Example 1, the sensor can be modified the way that at least two segments of distinctly different height $H_{knob}(i)$, i≥2, are present, Preferably, the segmentation is at least mirror-symmetrical in view of the about mirror-symmetrical movement of the lids.

FIG. 8 shows an arrangement with two large segments S0 51 which constitutes the first sensor. Between them two smaller segments S1 53 are provided, constituting sensor 2. They are characterized by a knob significantly lower than the knob of S0.

For the data transfer, two antennas 55, 56 are provided for sensor 51 resp. 53, each extending over the whole periphery. However, the antenna/sensor capacitor arrangements are responsive to different frequencies so that the sensors are capable to furnish data independently and without additional measures for avoiding conflicts.

Besides the antennas 55, 56, FIG. 9 also shows the differing heights $H_{knob,S0}$ 58 and $H_{knob,S1}$ 59.

The effect of the different knob elevations is depicted in FIG. 10. The points in time when sensor S1 53, too, gets in contact with the cornea or loses contact immediately defines the times $t_{trigger10}$ 61 and $t_{trigger11}$ corresponding to a well-defined indentation $H_{S0}$ by the sensor S0 51.

Furthermore, sensor S1 53 furnishes by itself a maximum quasi steady state force value 63 in addition to the maximum steady state value 62 of sensor s0 51.

In a first alternative, the force values $F_{max,S0}$ 62 and $F_{trigger,S0}$ 64 of sensor S0 at $t_{max}$ (eyelid closed, maximum force signal) resp. at $t_{trigger10}$ which is now a well-defined indentation depth by S0, are used. Additionally, or alternatively to the force signal of S0 at $t_{trigger10}$, the maximum force signal of the second sensor can be used. Another usable value is the force $F_{trigger1,S0}$ at $t_{trigger11}$, which is, however, more difficult to determine due to its more complicate history, yet because of the slower lid movement, the time resolution is better.

These values obtained at steady-state may be used for a linear extrapolation to H=0 yielding directly the true IOP as shown in FIG. 11. The straight line through pressure $p_{max,S0}$ 62 at $H_{knob,S0}$ 59 and pressure $p_{trigger}$ 64 at indentation $H_{knob,S0}-H_{knob,S1}$ 67 (indentation by sensor S0 when sensor S1 just touches the cornea) is extended to the ordinate to yield the true IOP 68.

In case of the values obtained at points in time ($t_{trigger10}$) where the indentation is changing, dynamic effects are to be taken in account, and by experience, a non-linear fit has to be performed on the basis of the biomechanical model as explained above.

The force or pressure values at $t_{trigger10}$ and $t_{trigger11}$ may be used to calculate the hysteresis parameter τ, too.

The concept is not limited to two sensors. Further sensors having different knobs may be provided, and the sizes of the sensors are not restricted to S1 being significantly smaller than S0.

Example 3

The knob is provided with a transition 70. In FIG. 12, the transition is a transition to a broader knob shape. In other terms, from the apex 72 to the transition 70, the shape of the knob corresponds to a small knob, and from transition 70 down to the membrane 7, the shape of the basis 71 corresponds to a bigger knob.

When the knob 14 is pressed on the cornea 22, the signals obtained are those as if the knob has the shape of the small knob (portion 73 in FIG. 13). If the indentation increases, the cornea gets in touch with the transition 70 at time $t_{trigger0}$ 74. As the contact zone is stepwise increased, also the force signal of the sensor shows a step increase 75. Afterwards, the signal 76 merely corresponds to that of a virtual bigger knob.

During opening of the eye, the same occurs in the inverse sense at $t_{trigger1}$ 77: The force signal shows a sharp decay 78 when the cornea no more touches the broader basis 71.

As shown in FIG. 14, the same effect may be obtained by a small knob shape 79 over one part of the sensor extension, and the remainder 80 being shaped as a significantly bigger knob. In this case, the transition zone is preferably wave-shaped so that a smooth transition occurs to avoid an irritation of the eye.

The resulting p/H diagram is shown in FIG. 15. Essentially the part 81 toward the closed eye is shifted to higher pressure values. Furthermore, the shift zone defines a pre-determined point in time, and the pressures $p_{trigger0}$ 83 and $p_{trigger1}$ 85 allow to determine the hysteresis τ.

The transition depth $H_{trigger}$ 87 once again defines a point in time where the indentation depth either corresponds to the apex 72 or the difference between greater knob height and smaller knob height in the variant of FIG. 14.

The pressure $p_{trigger0}$ 83 defines a pressure at indentation $H_{trigger}$ 87. The upwards shifted part 81 of the hysteresis curve is normalized or corrected by using the effective contact surface (the continuous line indicate a calculation assuming a uniform shape) yielding the curve 88 (dashed line).

The thereby obtained vertex point 90 is $p_{max}$ at $H_{knob}$, i.e. frame 5 in contact with the cornea 22. The two points obtained ($p_{trigger0}$ 83, $p_{max}$ 90) allow a linear extrapolation as explained above for FIG. 11 yielding the true IOP 63.

From the foregoing examples, the one skilled in the art is capable to conceive numerous variants and alterations without leaving the scope of the invention which is solely defined by the claims.

In particular, the following may apply:

With respect to Examples 2 and 3, there may be more knobs of different height or transitions, possibly even in combination, e.g. two knobs each with a transition. The advantage would be to have more points for determining the IOP by extrapolation.

Other mechanical models of the cornea may be used, e.g. the Standard Linear Solid model or models developed for soft tissue, e.g. M. N. Tanahq, M. Higashimori, M. Kaneko, I. Kao, IEEE Transactions on Biomedical Eng., 58/3 (2011), 509.

The contact lens may be made of other materials acceptable for being applied to the eye, in particular of pure silicon rubber.

GLOSSARY a acceleration (of the lid)
FEA Finite Element Analysis
$F_{max}$ maximum force
F(t), Fi force at time t, resp. ith force value
$F_{th}$ threshold value of sensor signal
H indentation depths of knob in the cornea
$H_{knob,max}$ height of the knob with respect to the surface of the sensor frame=maximal indentation
$H_{max}$ maximum indentation
$H_{trigger}$ a predefined indentation value
IOP intraocular pressure
$p_c$, $p_o$ pressure measured at a given indentation $H_{trigger}$ during eye closing resp. opening
$p_{cornea}$ pressure of cornea opposed to IOP
p(t), pi pressure dependent on time t, resp. ith pressure
$p_{trigger0/1}$ pressure at time $t_{trigger0/1}$
S0 segment with larger knob
S1 segment with smaller knob
$s_{lid}$ position of the lid
$t_{end}$ time when knob loses contact with cornea in lid opening
$t_{IOP1}$, $t_{IOP0}$ start time of lid opening, end time of lid closing
$t_{IOP0}$ time of passage of force signal through $F_{th}$ during lid closing; end time of lid closing
$t_{start}$ time when knob starts to exert pressure on the cornea, i.e. a force signal first occurs
$t_{trigger0,1}$ triggering times, where $H_{trigger0/1}$ occurs
v velocity (of the lid)
$v_{start}$ lid velocity at $t_{start}$

What is claimed is:

1. A method for monitoring biomechanical properties of an eye, using a measuring arrangement which comprises a measuring device worn in the manner of a contact lens, the measuring device comprising a force detector in operative engagement with a protrusion directed towards the cornea of the eye and configured to create an indentation of the cornea when the measuring device is applied to the eye, the measuring device having a flexible portion to be pressed against the cornea by a lid of the eye moving over the measuring device, wherein the method comprises the following steps:
measuring and storing force values and indications of times when the force values occurred;
determining the time $t_{start}$ when the force values start to be greater than zero, and the time $t_{End}$ at which the force values after $t_{start}$ are no longer greater than zero, which are equivalent respectively to the times when the protrusion first gets in contact with the cornea and disconnects therefrom;
determining a maximum force value between $t_{start}$ and $t_{End}$ in order to determine the phases of eye closing, eye being closed, and eye opening;
deriving from the force values and the corresponding time values between $t_{start}$ and $t_{End}$ a value indicative of the tension of the cornea.

2. The method of claim 1, wherein the indentation of the cornea created by the protrusion is dependent upon the position of the eye lid while closing or opening.

3. The method of claim 2, wherein the position of the lid is determined by applying a movement model based on constant acceleration or deceleration, the acceleration and deceleration values being selected in a set of predetermined values with either the length of the time between $t_{start}$ and the time when the maximum force occurs, or the length of time between $t_{End}$ and the time when the maximum force occurs, being used as the selection criterion.

4. The method of claim 1, wherein based on the maximum force value occurring between $t_{start}$ and $t_{End}$, a period of time $t_{IOP1}$ to $t_{IOP1}$ comprising the maximum force value is determined, in which the force values do not deviate more than 10% from the average of the force values in the period, and to determine an uncompensated intraocular pressure as the average of force values in the period, and to determine the cornea tension value using the measured force-time values with the values of the period $t_{IOP0}$ to $t_{IOP1}$ excised.

5. The method of claim 4, wherein the measuring device further comprises a rigid part which is disposed to abut the cornea when the lid of the eye is closed as to cause an indentation of the cornea which is given by the height $H_{knob,max}$ of the protrusion.

6. The method of claim 1, wherein the force values and the corresponding time values either directly or respectively derived values are inserted into a set of equations furnished by a model of the behaviour of the cornea, solving the set of equations by varying parameters of the model, and computing the tension of the cornea using the parameters.

7. The method of claim 1, wherein the shape of the protrusion is provided with at least one discontinuity so that at least one step in the force values is observed, with the at least one step being attributable to an indentation depth predefined by the discontinuity.

8. The method of claim 7, wherein an extrapolation is performed using at least two of the following measured value pairs:
maximum force and corresponding indentation depth; and
the pairs of force values and corresponding indentation depths defined by the at least one discontinuity.

9. The method of claim 8, wherein the at least one discontinuity comprises a transition from a smaller to a larger width of the protrusion transverse to a height thereof.

10. The method of claim 8, wherein the at least one discontinuity is provided by at least one additional protrusion of a different height than said first named protrusion.

11. The method of claim 4, in which the force values do not deviate more than 5% from the average of the force values in the period.

12. The method of claim 11, in which the force values do not deviate more than 2% from the average of the force values in the period.

13. The method of claim 8, wherein the extrapolation is a linear extrapolation toward indentation depth 0.

14. The method of claim 8, wherein the extrapolation is a non-linear fit.

* * * * *